United States Patent

Murata et al.

[11] 4,107,219
[45] Aug. 15, 1978

[54] PROCESS FOR PRODUCING CHAIN TERPENE ALCOHOL

[75] Inventors: Atsuo Murata; Shuji Tsuchiya; Hideo Suzuki; Hisao Ikeda, all of Funabashi, Japan

[73] Assignee: Nissan Chemical Industries Ltd., Tokyo, Japan

[21] Appl. No.: 795,789

[22] Filed: May 11, 1977

[30] Foreign Application Priority Data

May 14, 1976 [JP] Japan .................................. 51-54941

[51] Int. Cl.$^2$ ............................................. C07C 29/00
[52] U.S. Cl. .................................................. 568/875
[58] Field of Search ................. 260/631.5, 632, 617 R

[56] References Cited

PUBLICATIONS

Takabe et al., Chem. Abst., vol. 83, p. 411, #206433r (1975).
Cope et al., J.A.C.S., vol. 71, pp. 3423-3428 (1949).
Routenstrauch, Helv. Chim. Acta. vol. 56, pp. 2492-2508 (1973).
Takabe et al., Tetrahedron Litt., #34, pp. 3005-3006 (1975).
Fieser et al., Reagents for Organic Synthesis, pp. 723-730 (1964).

Primary Examiner—James O. Thomas, Jr.
Assistant Examiner—James H. Reamer
Attorney, Agent, or Firm—Oblon, Fisher, Spivak, McClelland & Maier

[57] ABSTRACT

A chain terpene alcohol having the formula

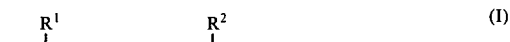
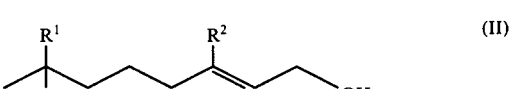

wherein $R^1$ and $R^2$ are the same or different and respectively represent hydrogen atom or a lower alkyl group is produced by oxidizing a chain unsaturated amine having the formula

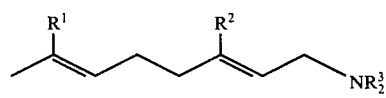
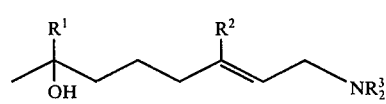

wherein $R^3$ represents an alkyl group and heating the product for a thermal rearrangement to form a chain unsaturated hydroxylamine having the formula

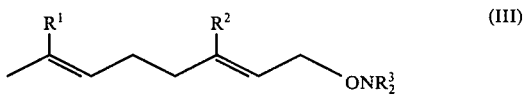
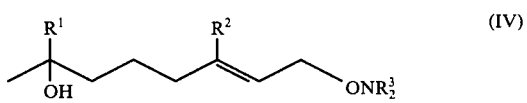

and then reducing the chain unsaturated hydroxylamine with hydrogen in the presence of a catalyst selected from the group consisting of iron family elements, copper family elements, oxides thereof and copper chromite.

7 Claims, No Drawings

PROCESS FOR PRODUCING CHAIN TERPENE ALCOHOL

BACKGROUND OF THE INVENTION

1. Field of the Invention

The present invention relates to a process for producing a chain terpene alcohol having the formula (I) or (II) by a hydrogenation of N,N-dialkyl hydroxylamine having the formula (III) or (IV) with hydrogen in the presence of a catalyst. More particularly, it relates to a process for producing a chain terpene alcohols such as geraniol, nerol, citronellol, hydroxygeraniol, hydroxynerol or hydroxycitronellol.

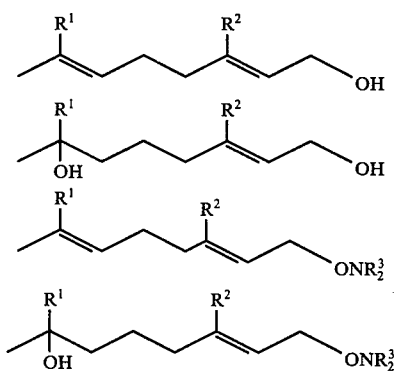

wherein $R^1$ and $R^2$ are the same or different and respectively represent hydrogen atom or a lower alkyl group and $R^3$ represents an alkyl group.

2. Description of the Prior Art

Heretofore, the cleavage reaction of hydroxylamine bond by a hydrogenation in the presence of a catalyst has been studied by using Pt catalyst. However, the cleavage reaction of hydroxylamine bonded to chain unsaturated hydrocarbons with hydrogen has not been studied.

Thus, in order to attain the cleavage of O—N bond by the selective hydrogenation, the methods of using the reducing reagents such as zinc-acetic acid have been proposed. However, from the viewpoint of pollution, the conventional reduction using the reducing reagent had industrial disadvantages of the treatment of the by-products and it was uneconomical reducing method.

The inventors have studied on the hydrogenation cleavage of O—N bond of hydroxylamines having chain unsaturated hydrocarbon group to obtain chain unsaturated terpene alcohols which had been considered to be impossible.

SUMMARY OF THE INVENTION

It is an object of the present invention to provide a process for producing chain terpene alcohols from N,N-dialkyl hydroxylamines.

Another object of the present invention is to provide a process for producing chain terpene alcohols such as geraniol, nerol, citronellol, hydroxygeraniol, hydroxynerol or hydroxycitronellol.

The other object of the present invention is to provide a process of cleavage of —O—N bond of N,N-dialkyl hydroxylamines with hydrogen without a rearrangement of double bond in the chain unsaturated hydrocarbon group under inhibiting hydrogenation of the unsaturated bond.

The foregoing and other objects have been attained by producing a chain terpene alcohol having the formula

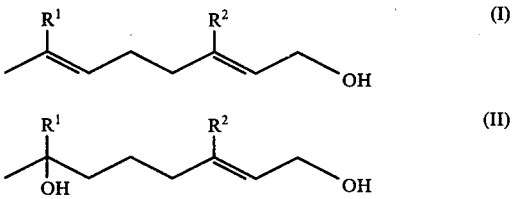

wherein $R^1$ and $R^2$ are the same or different and respectively represent hydrogen atom or a lower alkyl group by oxidizing a chain unsaturated amine having the formula

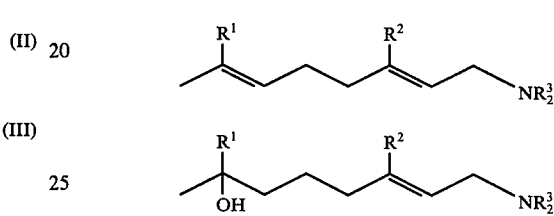

wherein $R^3$ represents an alkyl group and heating the product for a thermal rearrangement to form a chain unsaturated hydroxylamine having the formula

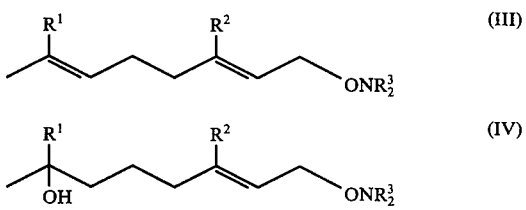

and then reducing the chain unsaturated hydroxylamine with hydrogen in the presence of a catalyst selected from the group consisting of iron family elements, copper family elements, oxides thereof and copper chromite.

DETAILED DESCRIPTION OF THE PREFERRED EMBODIMENTS

The catalysts used in the process of the present invention can be iron family elements, copper family elements, oxides thereof and copper chromite. The catalysts are suitable for the hydrogenation cleavage of the —O—N bond under remaining the unsaturated bonds.

Suitable catalysts include Raney catalysts obtained by the Raney development of aluminum alloy containing Ni, Co, Fe or Cu; Urushibara nickel catalysts having similar characteristics of Raney nickel, the reduced Ni, Co, Fe or Cu catalysts obtained by reducing a metal oxide prepared by a precipitation method from a water soluble metal salt with hydrogen, etc.

The oxide of Ni, Co, Fe or Cu can be also used as the catalysts for the hydrogenation cleavage of O—N bond.

The copper chromite catalysts (Cu-Cr catalyst; copper oxide-chromium oxide catalyst or Adkins catalyst) can be also used.

The catalysts suitable for the hydrogenation cleavage of O—N bond are used in various forms such as the suspension, the fixed bed, and others.

The amount of the catalyst is dependent upon the reaction activity of the catalyst and the starting material, the reaction temperature, hydrogen pressure, the form of the catalyst and the concentration of the starting material in the reaction system.

In order to attain the hydrogenation cleavage of O—N bond in the presence of the catalyst, it is preferable to use a solvent which dissolves the starting material of the N,N-dialkyl hydroxylamine and the product of the chain terpene alcohol, such as alcohols, ethers, hydrocarbons, etc. However, the reaction can be attained without a solvent.

The pressure of hydrogen and the reaction temperature in the hydrogenation are dependent upon the kinds of the catalysts.

When a nickel type catalyst is used, it is possible to hydrogenate at relatively low temperature such as 25° to 130° C, under relatively low pressure such as the atmospheric pressure to 70 kg/cm² G. When the pressure and the temperature are too high, the double bond is hydrogenated to increase citronellol and dimethyl octanol, etc.

When a copper type catalyst or a copper-chromite type catalyst is used, the velocity of hydrogenation is relatively slow and it is preferable to hydrogenate at relatively high temperature such as 50° to 150° C, under relatively high pressure such as 30 to 150 kg/cm² G. Even though the temperature and the hydrogen pressure are relatively high, the hydrogenation of the double bond is slight to form only small amount of citronellol and dimethyl octanol. The cobalt type catalysts have catalytic activity in the middle of those of the nickel type catalyst and the copper type catalyst. The iron type catalysts have lower catalytic activity. The temperature and the pressure are considered depending upon the catalytic activity.

After the hydrogenation cleavage, the catalyst is separated by a filteration etc. and the solvent and the by-product of dialkylamine are separated by a distillation and the unreacted N,N-dialkyl hydroxylamine and the object chain terpene alcohol are distilled out and are purified by a chromatography or other means in the batch system.

The resulting chain terpene alcohol can be further separated by means of fine distillation if necessary.

The by-product of dialkylamine can be used for the preparation of the N,N-dialkyl hydroxylamine or a solvent. The N,N-dialkyl hydroxylamine can be used for the hydrogenation. The catalyst can be also reused.

Thus, the chain terpene alcohols obtained by the present invention are geraniol, nerol, citronellol, hydroxygeraniol, hydroxynerol, hydroxycitronellol as the main components.

The N,N-dialkyl hydroxylamines having the formula (III) or (IV) can be obtained by a thermal rearrangement of the compound

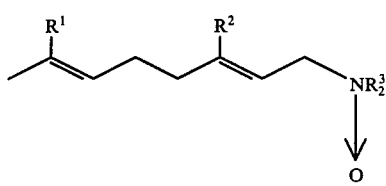

-continued

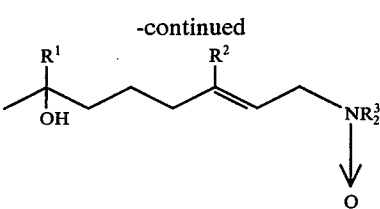

For example, O-(3,7-dimethyl-2,6-octadienyl)-N,N-dialkyl hydroxylamine or O-(3,7-dimethyl-7-hydroxy-2-octenyl)-N,N-dialkyl hydroxylamine can be prepared by various processes.

The process for producing them by using isoprene and an alkylamine is especially advantageous.

That is, O-(3,7-dimethyl-2,6-octadienyl)-N,N-dialkyl hydroxylamine can be obtained by reacting isoprene with a dialkylamine in the presence of a lithium catalyst such as metallic lithium or an organo-lithium compound to produce N,N-dialkyl-3,7-dimethyl-2,6-octadienylamine (mainly dialkyl neryl amine) and oxidizing it to produce N,N-dialkyl-3,7-dimethyl-2,6-octadienylamine oxide with a peroxide and heating it at 90° to 200° C to produce O-(3,7-dimethyl-2,6-octadienyl)-N,N-dialkyl hydroxylamine.

The N,N-dialkyl-3,7-dimethyl-2,6-octadienylamine can be also obtained by reacting myrcene with a dialkylamine in the presence of a catalyst of sodium, potassium or lithium.

O-(3,7-dimethyl-7-hydroxy-2-octenyl)-N,N-dialkyl hydroxylamine can be obtained by hydrolyzing N,N-dialkyl-3,7-dimethyl-2,6-octadienylamine (mainly dialkyl nerylamine) in the presence of hydrochloric acid or sulfuric acid to produce N,N-dialkyl (3,7-dimethyl-7-hydroxy-2-octene) amine and oxidizing it to produce N,N-dialkyl (3,7-dimethyl-7-hydroxy-2-octene) amineoxide and heating it at 90° to 200° C to produce O-(3,7-dimethyl-7-hydroxy-2-octenyl)-N,N-dialkyl hydroxylamine.

PREPARATION 1

Preparation of 3,7-dimethyl-2,6-octadienyl diethylamine (N,N-diethyl nerylamine)

In a glass reactor (100 cc) purged with nitrogen, 0.25 mole of isoprene, 0.05 mole of diethylamine, 0.005 mole of n-Bu-Li and 15 g of benzene were charged and the mixture was stirrier at 65° C for 8 hours to react them.

After the reaction, a small amount of ethanol was added to cease the reaction. The reaction products were measured by a gas chromatography.

As the result, the yield of N,N-diethyl nerylamine was 32.3% (based on isoprene) or 80.7% (based on diethylamine).

The conversion of isoprene was 38.5% and the selectivity of isoprene to N,N-diethyl nerylamine was 83.8%.

PREPARATION 2

Preparation of 3,7-dimethyl-2,6-octadienyl diethylamine (N,N-diethyl nerylamine)

In accordance with the process of Preparation 1 except using 0.25 mole of isoprene, 0.05 mole of diethylamine, 0.01 mole of metallic lithium and 15 g of benzene, the reaction was carried out at 65° C for 8 hours.

After the reaction, the reaction mixture was distilled to obtain the yield of 75.6% based on diethylamine. (Conversion of isoprene: 42.5%; selectivity of isoprene: 71.1%).

PREPARATION 3

Preparation of O-geranyl-N,N-diethyl hydroxylamine and O-neryl-N,N-diethyl hydroxylamine N,N-diethyl nerylamine oxide was obtained by adding 19.2 ml of 30% hydrogen peroxide and 24 ml of methanol to 7.44 g of N,N-diethyl nerylamine of Preparation 1. (Reaction at 65° C for 4 hours)

A 2.4 g of N,N-diethyl nerylamine oxide was mixed with 10 ml of benzene and the mixture was heated at 115° to 125° C for 3 hours and the reaction mixture was distilled to obtain hydroxylamine mixture (HA) of 68 mole % of O-geranyl-N,N-diethyl hydroxylamine (GHA) and 32 mole % of O-neryl-N,N-diethyl hydroxylamine (NHA) in the yield of 81% based on N,N-diethyl nerylamine.

PREPARATION 4

In accordance with the process of Preparation 1, except using 9.9 g of myrcene, 3.6 g of diethylamine and 0.1 g of metallic sodium, the reaction was carried out at 40° C for 3 hours.

After the reaction, the reaction mixture was distilled to obtain 7.7 g of N,N-diethyl geranylamine (boiling point: 85° to 87° C/2 mmHg).

In accordance with the Preparations 2 and 3, N,N-diethyl geranylamine was oxidized and rearranged to obtain O-neryl-N,N-diethyl hydroxylamine and O-geranyl-N,N-diethyl hydroxylamine.

PREPARATION 5

In 100 cc autoclave made of stainless steel (under pressure) or 100 cc glass flask (atmospheric pressure) as the reactor, a mixture of O-geranyl-N,N-diethyl hydroxylamine and O-neryl-N,N-diethyl hydroxylamine which was obtained in Preparation 3 was hydrogenated with hydrogen in a solvent of ethyl alcohol in the conditions of Table 1 with stirring.

After the reaction, each reaction mixture was filtered and distilled to separate the catalyst and the solvent. The unreacted hydroxylamine, geraniol, nerol and citronellol and the others in the reaction product were measured by a gas chromatography in the standardization (20% PEG 20 M, 1 m glass column, 100 → 180° C: 4° C/min.; 50 ml He/min.).

The following catalysts were used.

Raney Catalysts

Each alloy of aluminum and other metal was developed with a base by the conventional method (W-4) and the product was washed and stored in ethanol.

Other Catalysts

Manufactured by Nissan-Girdler.

Table 1

| No. | Catalyst | Amount ① | $H_2$ pressure (kg/cm$^2$G) | Temp. (° C) | Time (hr.) | Amount of solvent ② |
|---|---|---|---|---|---|---|
| 1 | Raney Ni | 0.20 | NP | 25 | 8.5 | 0.07 |
| 2 | " | 0.062 | NP | 60 | 3 | 0.07 |
| 3 | Reduced Ni | 0.15 | 10 | 115 | 1 | 0.05 |
| 4 | Raney Co | 0.2 | 30 | 80 | 8 | 0.05 |
| 5 | " | 0.44 | 50 | 50–80 | 4.5 | 0.02 |
| 6 | Reduced Co | 0.44 | 50 | 80 | 6 | 0.02 |
| 7 | Raney Fe | 1.1 | 50 | 80 | 5 | 0.02 |
| 8 | Raney Cu | 0.44 | 50 | 80 | 5 | 0.02 |
| 9 | Reduced Fe | 2.0 | 50 | 120 | 7 | 0.02 |
| 10 | Reduced Cu | 0.2 | 50 | 100 | 1 | 0.04 |
| 11 | Oxidized Cu | 0.5 | 50 | 105 | 3 | 0.025 |
| 12 | Cu chromite | 0.44 | 50 | 80 | 3 | 0.02 |
| 13 | " | 0.1 | 70 | 120 | 1.5 | 0.033 |
| 14 | " | 0.1 | 80 | 120 | 1.0 | 0.03 |
| 15 | Raney Cu | 0.44 | 50 | 80 | 4.5 | 0.02 |
| 16 | Raney Cu | 0.44 | 50 | 80 | 4.5 | 0.02 |
| 17 | Cu Chromite | 0.25 | 50 | 110 | 2.0 | 0.3 |
| 18 | Raney Ni | 0.1 | 30 | 80 | 4 | — |
| 19 | Cu chromite | 0.1 | 70 | 120 | 6.5 | — |
| 20 | " | 0.25 | 50 | 115 | 1.5 | 0.3 |
| Ref. 1 | Pt2%/Al$_2$O$_3$ | 0.3 | 50 | 80 | 7.5 | 0.02 |
| Ref. 2 | " | 1.1 | 50 | 80 | 5.5 | 0.02 |
| Ref. 3 | Pd5%/C | 0.044 | 50 | 80 | 1 | 0.02 |
| Ref. 4 | Pd5%/Al$_2$O$_3$ | 0.58 | 50 | 80 | 3 | 0.02 |
| Ref. 5 | Pd5%/C | 0.89 | 50 | 80 | 5 | 0.02 |
| Ref. 6 | Rh5%/C | 0.67 | 50 | 80 | 4 | 0.02 |

NP = normal pressure

Table 1'

| No. | Conversion ③ (mole %) | Terpene alcohol Yield (mole %) | | | | Selectivity ⑦ (%) | By-product | | | Remarks |
|---|---|---|---|---|---|---|---|---|---|---|
| | | N.OH ④ | G.OH ⑤ | C.OH ⑥ | Total | | I ⑧ | II ⑨ | Other amine ⑩ | |
| 1 | 80 | 23 | 50 | 6 | 79 | 98 | — | — | — | |
| 2 | 43 | 11 | 30 | 1 | 42 | 98 | — | — | — | |
| 3 | 95 | 28 | 55 | 12 | 95 | 100 | — | — | — | |
| 4 | 50 | 9 | 19 | 20 | 48 | 96 | — | — | — | |
| 5 | 76 | 5 | 11 | 42 | 58 | 76 | — | *1 | :1 | |
| 6 | 50 | 10 | 23 | 11 | 44 | 90 | — | — | — | |
| 7 | 100 | 27 | 56 | 12 | 95 | 95 | — | — | — | |
| 8 | 70 | 20 | 43 | 2 | 65 | 92 | — | — | — | |
| 9 | 10 | 3 | 7 | — | 10 | 100 | — | — | — | |
| 10 | 92 | 30 | 61 | 1 | 92 | 100 | — | — | — | |
| 11 | 100 | 31 | 61 | 6 | 98 | 98 | — | — | — | |
| 12 | 96 | 36 | 57 | 5 | 96 | 100 | — | — | — | |
| 13 | 96 | 34 | 60 | 2 | 96 | 100 | — | — | — | |
| 14 | 94 | 34 | 57 | 0.25 | 92 | 98 | — | — | — | *5 |
| 15 | 10 | 3 | 7 | — | 10 | 100 | — | — | — | *6 |
| 16 | 21 | 7 | 12 | 2 | 21 | 100 | — | — | — | *7 |
| 17 | 97 | 30 | 60 | 3.2 | 93 | 96 | — | — | — | *8 |
| 18 | 65 | 19 | 32 | 14 | 65 | 100 | — | — | — | *9 |
| 19 | 44 | 15 | 28 | 1 | 44 | 100 | — | — | — | *9 |
| 20 | 97 | 29 | 57 | 6.7 | 90.7 | 95 | — | — | — | *10 |
| Ref. 1 | 10–20 | ~3 | ~7 | ~5 | ~15 | — | — | — | *1 | |
| Ref. 2 | 80–90 | — | — | — | — | — | *1 | *1 | *2 | |
| Ref. 3 | 100 | — | — | — | — | — | *4 | *2 | *1 | |
| Ref. 4 | 20–30 | — | — | — | — | — | — | *1 | *1 | |
| Ref. 5 | 100 | — | — | — | — | — | *2 | *1 | *4 | |

Table 1'-continued

| No. | Conversion ③ (mole %) | Terpene alcohol Yield (mole %) | | | | Selectivity ⑦ (%) | By-product | | | Remarks |
|---|---|---|---|---|---|---|---|---|---|---|
| | | N.OH ④ | G.OH ⑤ | C.OH ⑥ | Total | | I ⑧ | II ⑨ | Other amine ⑩ | |
| Ref. 6 | 100 | — | — | — | — | — | *2 | *3 | *1 | |

*1 The by-product was found
*2 The by-product was main component
*3 The by-product was found in high ratio
*4 The by-product was found in low ratio
*5 R₃: methyl group
*6 Solvent: dioxane
*7 Solvent: cyclohexane
*8 Solvent: isostearyl alcohol
*9 Any solvent was not used
*10 Solvent: benzene
Note:
1) Scale NHA + GHA 0.89 g (NHA/GHA = 1/2.08)
2) Catalysts of Ref. 1, 2, 5, 6 manufactured by Nippon Engelhard K.K.
3)

① $\dfrac{\text{catalyst (g)}}{\text{charged hydroxylamine (g)}}$

② $\dfrac{\text{charged hydroxylamine (g)}}{\text{ethanol (g)}}$

③ $\dfrac{\text{charged HA} - \text{unreacted HA}}{\text{charged HA}} \times 100$ ④ nerol
⑤ geraniol
⑥ citronellol ⑦ $\dfrac{\text{terpene alcohol yield}}{\text{conversion}} \times 100$

⑧

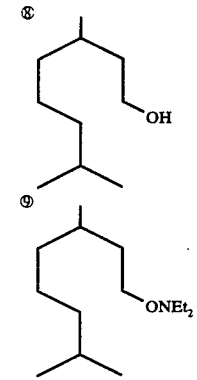

⑨

⑩ components extracted with 2N—HCl
NHA: O-neryl-N,N-diethyl hdyroxylamine
GHA: O-geranyl-N,N-diethyl hydroxylamine
HA: total hydroxylamines

PREPARATION 6

Preparation of N,N-diethyl (3,7-dimethyl-7-hydroxy-2-octenyl) amine

In a glass reactor (100 cc) purged with nitrogen, 0.5 mole of isoprene, 0.1 mole of diethylamine, 0.01 mole of n-Bu-Li and 30 g of benzene were charged and the reaction was carried out at 65° C for 8 hours with stirring.

After the reaction, a small amount of ethanol was added to cause the reaction. The reaction products were measured by a gas chromatography.

As a result, the yield of N,N-diethyl nerylamine was 80.7% based on diethylamine.

A 15 g of N,N-diethyl nerylamine was mixed with 80 cc of 3N-HCl, and the reaction was carried out at 45° C for 5 hours with stirring to obtain N,N-diethyl (3,7-dimethyl-7-hydroxy-2-octenyl) amine (boiling point 115° to 117° C/3 mmHg) in the yield of 95%.

PREPARATION 7

Preparation of O-(3,7-dimethyl-7-hydroxy-2-octene) N,N-diethyl hydroxylamine N,N-diethyl (3,7-dimethyl-7-hydroxy-2-octenyl) amine oxide was obtained by adding 20 cc of 35% hydrogen peroxide and 30 cc of methanol to 13 g of N,N-diethyl (3,7-dimethyl-7-hydroxy-2-octenyl) amine of Preparation 6. (Reaction at 65° C for 4 hours)

A 13 g of N,N-diethyl (3,7-dimethyl-7-hydroxy-2-octenyl) amine oxide was mixed with 70 cc of toluene and the mixture was stirred at 115° C for 4 hours and the reaction mixture was distilled to obtain O-(3,7-dimethyl-7-hydroxy-2-octene) N,N-diethyl hydroxylamine (boiling point: 120° to 125° C/1.5 mmHg) in the yield of 80%.

PREPARATION 8

In 100 cc autoclave made of stainless steel, 1.0 g of O-(3,7-dimethyl-7-hydroxy-2-octene) N,N-diethyl hydroxylamine of Preparation 7, 0.3 g of Raney nickel and 40 g of ethanol were charged and a hydrogenation was carried out at an initial pressure of hydrogen of 5 kg/cm² for 3 hours.

The catalyst was separated and the reaction mixture was distilled to obtain 3,7-dimethyl-2-octene-1,7-diol (boiling point: 105° to 109° C/0.45 mmHg) in the yield of 89 mole % and 3,7-dimethyl octane-1,7-diol (boiling point: 102° to 105° C/0.45 mmHg) in the yield of 8 mole %.

According to a gas chromatography analysis of the former product, it was found that the product was a mixture of hydroxy geraniol and hydroxy nerol at a ratio of 2 : 1.

PREPARATION 9

In accordance with the process of Preparation 8, except using various catalysts instead of Raney nickel, each hydrogenation of O-(3,7-dimethyl-7-hydroxy-2-octene) N,N-diethyl hydroxylamine of Preparation 7 was carried out in the conditions shown in Table 2.

Table 2

| Preparation | Catalyst | Amount of catalyst (%) ** | $H_2$ pressure $(kg/cm^2G)$ | Temperature (° C) | Time (hr.) | Conversion (mole %) | Yield (mole %) hydroxy geraniol hydroxy nerol | Yield (mole %) hydroxy citronellol |
|---|---|---|---|---|---|---|---|---|
| 9-1 | Raney-Co | 50 | 30 | 100 | 10 | 80 | 46 | 34 |
| 9-2 | Raney-Fe | 100 | 50 | 80 | 5 | 90 | 75 | 11 |
| 9-3 | Reduced Ni | 30 | 10 | 115 | 1 | 97 | 80 | 7 |
| 9-4 | Oxidized Cu | 20 | 50 | 115 | 1.5 | 97 | 90 | 3 |
| 9-5 | Cu chromite | 20 | 50 | 115 | 1 | 98 | 71 | 10 |
| 9-6 | *(non-solvent) | 20 | 50 | 115 | 6 | 40 | 38 | 1 |
| 9-7 | Pd/Af$_2$O$_3$ | 2 | 10 | 115 | 2 | 100 | 8 | 14 |

Note:
1) * 9-6: none solvent others: 40 g of ethanol per 1 g of starting material.
2) Catalyst:
Pd/Al$_2$O$_3$: 5% Pd on γ-Al$_2$O$_3$ manufactured by Nippon Engelhard K.K. Others are the same with those of Preparation 5.

** $\frac{Cat. (g)}{Charged\ starting\ material} \times 100$

What is claimed is:

1. A process for producing a chain terpene alcohol having the formula:

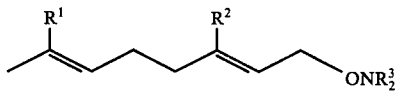   (I)

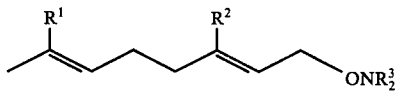   (II)

wherein $R^1$ and $R^2$ are the same or different and respectively represent hydrogen atom or a lower alkyl group which comprises oxidizing a chain unsaturated amine having the formula:

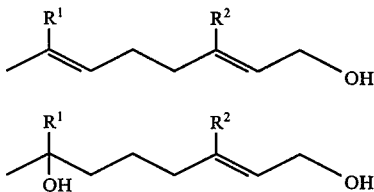

wherein $R^3$ represents an alkyl group to form the corresponding amine oxide, heating said amine oxide to effect a thermal rearrangement to form a chain unsaturated hydroxylamine having the formula:

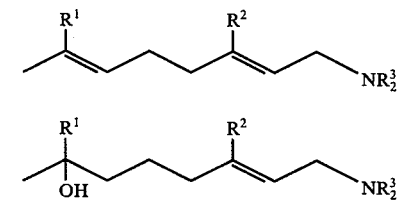

and then, reducing the chain unsaturated hydroxylamine with hydrogen in the presence of a catalyst selected from the group consisting of metallic iron, cobalt, nickel, copper, oxides thereof, and copper chromite.

2. A process for producing a chain terpene alcohol according to claim 1 wherein $R^1$ and $R^2$ respectively represent methyl group and $R^3$ represents ethyl group.

3. A process for producing a chain terpene alcohol according to claim 1, wherein said chain unsaturated amine is N,N-diethyl 3,7-dimethyl-2,6-octadienylamine or N,N-diethyl 3,7-dimethyl-7-hydroxy-2-octenylamine.

4. A process for producing a chain terpene alcohol according to claim 1 wherein said chain terpene alcohol is geraniol, nerol or citronellol.

5. A process for producing a chain terpene alcohol according to claim 1 wherein said chain terpene alcohol is hydroxygeraniol, hydroxynerol or hydroxycitronellol.

6. A process for producing a chain terpene alcohol according to claim 1 wherein said catalyst is selected from the group consisting of Raney nickel, Raney cobalt, Raney iron, Raney copper, reduced nickel, reduced cobalt, reduced iron, and reduced copper.

7. A process for producing a chain terpene alcohol according to claim 1 wherein said catalyst is selected from the group consisting of oxides of Cu, oxides of Ni, oxides of Co and copper chromite.

* * * * *